US008084212B2

(12) United States Patent
Ong et al.

(10) Patent No.: US 8,084,212 B2
(45) Date of Patent: Dec. 27, 2011

(54) **ASSAY FOR *MYCOBACTERIUM AVIUM/INTRACELLULARE* NUCLEIC ACID**

(75) Inventors: Edgar Ong, San Diego, CA (US);
Maurice Exner, Mission Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 12/887,403

(22) Filed: Sep. 21, 2010

(65) Prior Publication Data

US 2011/0027792 A1      Feb. 3, 2011

Related U.S. Application Data

(63) Continuation of application No. 11/338,431, filed on Jan. 23, 2006, now Pat. No. 7,824,858.

(51) Int. Cl.
*C12Q 1/68* (2006.01)
*C12P 19/34* (2006.01)
*C07H 19/34* (2006.01)

(52) U.S. Cl. ............... 435/6.15; 435/6.11; 536/23.7; 536/24.32; 536/24.33

(58) Field of Classification Search ................. None
See application file for complete search history.

(56) References Cited

U.S. PATENT DOCUMENTS

| | | | |
|---|---|---|---|
| 5,135,717 | A | 8/1992 | Renzoni et al. |
| 5,538,848 | A | 7/1996 | Livak et al. |
| 5,580,990 | A | 12/1996 | Van Den Berg et al. |
| 5,652,099 | A | 7/1997 | Conrad |
| 5,691,146 | A | 11/1997 | Mayrand |
| 5,714,327 | A | 2/1998 | Houthoff et al. |
| 5,723,591 | A | 3/1998 | Livak et al. |
| 5,736,333 | A | 4/1998 | Livak et al. |
| 5,866,336 | A | 2/1999 | Nazarenko et al. |
| 5,876,930 | A | 3/1999 | Livak et al. |
| 5,952,202 | A | 9/1999 | Aoyagi et al. |
| 5,985,566 | A | 11/1999 | Houthoff et al. |
| 6,030,787 | A | 2/2000 | Livak et al. |
| 6,136,529 | A | 10/2000 | Hammond |
| 6,258,569 | B1 | 7/2001 | Livak et al. |
| 6,268,132 | B1 | 7/2001 | Conrad |

FOREIGN PATENT DOCUMENTS

EP          0 539 466 B1      11/1996

OTHER PUBLICATIONS

Ellingson, J.L.E. et al. Molecular and Cellular Probes 14:153-161 (2000).*
Beggs, M.L. et al. Journal of Clinical Microbiology 38(2):508-512 (2000).*
Koivula, T. et al. Microbes and Infection 6:1320-1325 (2004).*
Fang, Z. et al. Journal of Bacteriology 181:1014-1020 (1999).*
Aoki et al, "Efficacy of PCR-microwqell plate hybridization method (Amplicor *Mycobacterium*) for detectin of *M. tuberculosis*, *M avium* and/or *M. intracellulare* in clinical specimens" Kekkaku, 69(10): 593-605, 1994. abstract only.
Beutler, et al., "Interference of Heparin with the Polymerase Chain Reaction", BioTechniques 9:166, 1990.
Bruijnesteijn van Coppenraet, et al., "Real-Time PCR Assay Using Fine-Needle Aspirates and Tissue Biopsy Specimens for Rapid Diagnosis of Mycobacterial Lymphadenitis in Children", J. Clin. Microbiol. 42(6): 2644-50, 2004.
Buck, et al., "Rapid, Simple Method for Treating Clinical Specimens Containing *Mycobacterium tuberculosis* to Remove DNA for Polymerase Chain Reaction" J. Clin. Microbiol. 30:1331-1334 (1992).
Cousins et al., "Multiplex PCR provides a low-cost alternative to DNA probe methods for rapid identification of *Mycobacterium avium* and *Mycobacterium intracellulare*", Journal of Clinical Microbiology, 34(9): 2331-2333, 1996.
Devallois discordant sequencing, et al., "Molecular characterization of *Mycobacterium avium* complex isolates giving discordant results in AccuProbe tests by PCR-restriction enzyme analysis, 16S rRNA gene sequencing, and DT1-DT6 PCT", Journal of Clinical Microbiology, 35(11): 2767-2772, 1997.
Ellingson et al, Evaluation of the accuracy and reproducibility of a practical PCR panel assay for rapid detection and differentiation of *Mycobacterium avium* supspecies, Mol Cell Probes, (2000), 14:153-161.
Guerrero et al, A novel insertion element from *Mycobacterium avium*, IS1245, is a specific target for analysis of strain relatedness, J Clin Microbio, (1995), 33(2):304-307.
Hafner, et al., Isothermal Amplification and Multimerization of DNA by Bst DNA Polymerase, Biotechniques Apr. 2001;30(4):852-867.
Henegariu, "Custom fluorescent nucleotide synthesis as an alternative method for nucleic acid labeling", Nat. Biotechnol. 18:345-348, 2000.
Ikonomopoulos et al., "Multiplex PCR assay for the detection of mycobacterial DNA sequences directly from sputum", In Vivo, 12(5): 547-552, 1998 (abstract).
Inderlied, et al., "The *Mycobacterium avium* Comples", Clin Microbiol Rev 6:266-310, 1993.
Jameson and Eccleston, "Fluorescent Nucleotide Analogs: Synthesis and Applications", Meth. Enzymol. 278:363-390, 1997. Koivula et al, Genetic diversity in clinical isolates of *Mycobacterium avium* complex from Guinea-Bissau, West Africa, Microbes Infect, (2004), 6:1320-1325.
Kulski et al., "Use of a multiplex PCR to detect and identify *Mycobacterium avium* and *M. intracellulare* in blood culture fluids of AIDS patients", Journal of Clinical Microbiology, 33(3): 668-674, 1995.
Kulski, et al., "Preparation of Mycobacterial DNA from Blood Culture Fluids by Simple Alkali Wash and Heat Lysis Method for PCR Detection", Journal of Clinical Microbiology 34: 1985-91, 1996.
Mansfield, "Nucleic acid detection using non-radioactive labeling methods", Mol. Cell. Probes 9:145-156, 1995.
Menendez et al., "Characterization of a *Mycobacterium intracellulare* Variant Strain by Molecular Techniques" J. Clin. Microbiol. 39:4241-46, 2001.
Meyer et al., "The Macrophage-induced gene mig as a marker for clinical pathogenicity and in vitro virulence of *Mycobacterium avium* complex strains", Infection and Immunity, 66(9): 4549-4552, 1998.
Motiwala et al., "Molecular Epidemiology of *Mycobacterium avium* subsp. *Paratuberculosis* Isolates Recovered from Wild Animal Species", Journal of Clinical Microbiology, 42(4): 1703-1712, 2004.
Plum et al., Cloning, Sequencing, and Expression of the mig Gene of *Mycobacterium avium*, Which Codes for a Secreted Macrophage-Induced Protein, Infection and Immunity, 65 (11): 4548-4557, 1997.

(Continued)

*Primary Examiner* — Diana Johannsen
(74) *Attorney, Agent, or Firm* — Foley & Lardner LLP

(57) ABSTRACT

Disclosed is a method for determining the presence of *Mycobacterium avium* complex nucleic acids in a biological sample. In particular, the IS1245 gene of *M. avium* and the DT1 gene of *M. intracellulare* are detected, preferably following amplification. In addition, the method distinguishes between species of *M. avium* and *M. intracellulare*. Also described are oligonucleotides that can be used as primers to amplify target genes such as IS1245 and DT1 genes and as probes as well as kits containing the oligonucleotides.

22 Claims, 4 Drawing Sheets

OTHER PUBLICATIONS

Plum et al., "Induction of *Mycobacterium avium* Gene Expression Following Phagocytosis by Human Macrophages", Infection and Immunity, 62 (3): 476-483, 1994.

Saiki, "Amplification of Genomic DNA in PCR Protocols", Innis et al., Eds., Academic Press, San Diego, CA 1990, pp. 13-20.

Shrestha et al., "Detection and Differentiation of *Mycobacterium tuberculosis* and Nontuberculous Mycobacterial Isolates by Real Time PCR", Journal of Clinical Microbiology, 41(11): 51215126, 2003.

Sola et al., "Molecular Characterization of *Mycobacterium avium* Complex Isolates from Caribbean Patients by DT1/DT6-PCR, Non-radioactive Southern Hybridization, and Accuprobe System", Current Microbiology, 33, 352-358, 1996.

Thierry et al, "Rapid Identification of *Myco bacterium avium-intracellulare* Complex Strains: Clinical Practice Evaluation of DT6 and DT1 Probes", Journal of Infectious Diseases, 168:1337-8, 1993.

Tortoli et al., "Performance Assessment of New Multiplex Probe Assay for identification of Mycobacteria", Journal of Clinical Microbiology, 39(3): 1079-1084, 2001.

Tyagi et al, Multicolor molecular beacons for allele discrimination, Nature Biotechnology, 16:49-53, (1998).

US Notice of Allowance dated Jul. 6, 2010 in U.S. Appl. No. 11/338,431.

US Office Action dated Mar. 31, 2010 in U.S. Appl. No. 11/338,431.

US Office Action dated Aug. 18, 2008 in U.S. Appl. No. 11/338,431.

Wharam et al., Specific Detection of DNA and RNA Targets Using a Novel Isothermal Nucleic Acid Amplification Assay Based on the Formation of a Three-Way Junction Structure, Nucleic Acids Res. 29(11):e54, 8 pgs, (2001).

Wilton and Cousins, "Detection and identification of multiple mycobacterial pathogens by DNA amplification in a single tube", PCR Methods Application, 1(4): 269-273, 1992. (abstract).

Yamori, et al., "Comparison of Prognosis of Pulmonary Diseases Caused by *Mycobacterium avium* and by *Mycobacterium intracellulare*", Chest 102:89-90, 1992.

Zhu, "Directly labeled DNA probes using fluorescent nucleotides with different length linkers", Nucl. Acids Res. 22:3418-3422, 1994.

\* cited by examiner

| | |
|---|---|
| 1 | GGATCCGCTG TGGACCGTCG CCGCCCGGCA CGTCGAGGAC GCCTGCGCGG TGCTGGACGG |
| 61 | CCACCAGGTT CCCGAAGGCG TGTCGCCGGC CGGGCGGGTC ATCGAACTGC CCGGCCTCGG |
| 121 | CCACCCGCTG CTGCCGCCGT GGACCGTCGC CGACTCCGGC GCGCACGGCG TCACCATGCA |
| 181 | GGGGCATTTC ACCCGATCGC ACGTGGGCGG CAACAACGCC GTGCACGGCG CATGATCCC |
| 241 | GCTCTACTAC GACTGGCTGT TCGGCATGGT GGTGTCCGGC GCGAACTGTC CACCCACGCG |
| 301 | CACCGCCTTC CTACACGTGG ATTACCGCAA CGTCACCCCG ATCGACGCGC CGCTGACGGC |
| 361 | GCACGGCCGC ATCACCGACG TCGACGGCCG CAAGATCTTC ATCTCCGCTA GCATGACGGC |
| 421 | GGCCGACGGC ACGCTGCTCA GTGAGGCCAC CGGCCTGATG GTCCGCCTGC TACCCCACCA |
| 481 | GCCGTGAGAG GCAAGATGTC CGACACCACA ACAGCATTCA CGGTACCGGC GGTCGCGAAG |
| 541 | GCCGTCGCGG CCGCGATTCC CGACCGCGAG CTGATCATCC AGGGCGACCG TCGCTACACC |
| 601 | TACCGGCAGG TGATCGAACG GTCGAACCGG CTCGCCGCGT ATCTGCACTC CCAGGGTCTG |
| 661 | GGATGCCACA CCGAGCGCGA GGCGCTGGCC GGCCACGAGG TGGGCCAGGA CCTGCTCGGC |
| 721 | CTCTACGCGT ACAACGGGAA CGAATTCGTC GAAGCGCTGC TGGGCGCCTT CGCTGCGCGC |
| 781 | GTCGCCCCGT TCAACGTCAA CTTCCGCTAC GTCAAAAGCG AACTGCACTA CCTGCTCGCG |
| 841 | GACTCCGAGG CGACCGCGCT GATCTACCAC GCGGCGTTCG CGCCCCGGGT GGCCGAGATC |
| 901 | CTGCCCGAGC TGCCGCGGCT TCGGGTGCTC ATCCAGATCG CCGACGAGTC GGGCAACGAA |
| 961 | TTACTCGACG GCGCAGTGGA TTACGAGGAC GCGCTGGCGT CGGTGTCCGC GCAGCCACCA |
| 1021 | CCGGTGCGGC ACTGTCCGGA CGACCTGTAC GTGCTGTACA CCGGCGGCAC CACGGGAATG |
| 1081 | CCCAAGGGCG TGTTGTGGCG TCAGCACGAC ATCTTCATGA CATCCTTCGG GGGGCGCAAC |
| 1141 | CTGATGACCG GCGAGCCCTC GTCGTCGATC GACGAGATCG TGCAGCGCGC CGCGTCTGGC |
| 1201 | CCGGGGACCA AGCTGATGAT CCTGCCGCCG CTGATCCACG GCGCGGCCCA GTGGAGCGTG |
| 1261 | ATGACGGCGA TCACGACCGG CCAGACGGTC GTCTTCCCCA CTGTCGTCGA CCATTTGGAC |
| 1321 | GCCGAGGACG TGGTGCGCAC CATCGAGCGG GAAAAGGTCA TGGTGGTGAC GGTGGTGGGT |
| 1381 | GACGCGATGG CGCGCCCGTT GGTCGCGGCC ATCGAGAAGG GGATCGCCGA CGTGTCGTCG |
| 1441 | CTGGCCGTGG TGGCCAACGG CGGCGCGTTG CTGACCCCGT TCGTCAAGCA GCGCTTGATC |
| 1501 | GAGGTGCTGC CGAACGCGGT GGTCGTCGAC GGCGTCGGGT CGTCGGAGAC CGGGGCGCAG |
| 1561 | ATGCACCACA TGTCGACGCC CGGGGCGGTG GCGACCGGCA CCTTCAACGC CGGCCCGGAC |
| 1621 | ACCTTCGTGG CGGCCGAGGA CCTGTCGGCG ATCCTGCCGC CGGGCACGA GGGGATGGGC |
| 1681 | TGGTTGGCCC AGCGCGGCTA TGTCCCGCTC GGGTACAAGG GCGATGCCGC CAAGACCGCC |
| 1741 | AAGACCTTTC CGGTCATCGA CGGGGTGCGC TACGCGGTGC CGGGCGACCG GCACGCCAC |
| 1801 | CACGCCGACG GCCATATCGA GCTGCTGGGC CGCGACTCCG TGTGCATCAA TTCCGGCGGC |
| 1861 | GAGAAGATTT TCGTCGAGGA GGTCGAGACG GCCATCGCGT CGCATCCCGC GGTGGCCGAC |
| 1921 | GTGGTGGTGG CCGGACGGCC GAGTGAACGG TGGGGCCAGG AAGTCGTCGC CGTGGTCGCG |

FIGURE 1

```
1981 CTGTCCGACG GCGCTGCCGT CGACGCCGGA GAATTGATCG CCCACGCATC GAATTCGCTG
2041 GCGCGCTACA AGCTTCCCAA GGCGATCGTG TTCCGTCCGG TGATCGAGCG CAGCCCGTCG
2101 GGCAAGGCCG ATTACCGGTG GGCGCGCGAG CAGGCGGTGA ACGGATGAAA CCCGCTGGGG
2161 CCGAGCGCTT TTAGGCTAGG AGCACACCGA TGAAGTACCA AGGGCGGGTC GCGGTGGTCA
2221 CGGGCGCCGG CTCGGGCATC GGCCGGGCGC TGACGCAGGC GCTCACCGCG GGCGGCGCGC
2281 ATGTCGCGGC GTCCGACATC GACGACAACG GCCTGGCCGA AACCCAGGCG TCGTGCGGTC
2341 CCGGACAGGT CACGCCATAT CGCGTCGACG TGGCGGACCG GGATGCGGTG CTGGGCTTCG
2401 CCGATGAGGT GCGCCGCAAG CACGGACCCG CCTCGATGGT GTTCAACAAC GCCGGCGTCG
2461 ACCTGTTCGC CAGCGTGGCC GACATGTCCT GGGAGAACTT CGACTGGCTG ATGGGCATCA
2521 ACGTCGGCGG TGTGGTCAAC GGGACCAAAG CCTTTCTGCC GCAACTCATC GAAGCCGGCT
2581 CCGACCGGCG GCCGTCGCGG TTGGTCAACC TGTCCAGCGC CTTCGGTCTC ATCGCGGTCC
2641 CCTACCAAGG GGCCTACAGC ACGTCGAAGT TCGCGGTGCG CGGATTCACG GAGGCCCTGC
2701 GCCAGGAGAT GATCATCGAA CGCCATCCGG TGACGGTGCA CTGCGTGCAC CCCGGAGTCG
2761 TGCGTACCAA CTTCGGCGCC AACATGCGCA CCTCGGACAC CGAGGATCC
```

FIGURE 1 (cont'd)

```
   1 GGAGCGTCCC GGGGAGTGGT GTAAGTGATG GCGCGTGTCG GTCCCTGACG TAAGAGGGCC
  61 ATCCGCGTGA GTCTCTGTGG TGAAACGACC AAGAATCACT ACCGAGAGGA ACATCGCGAT
 121 GGCCCTGGAC CAGTCTGCCT TGCTGGAGGT GCTCGACGCA CTGCGCACCG CCGATGCCGG
 181 TGAGCGGATC ACTCAAGCCG CCGAAACGAT CTACCAAGCC TTGATCGACG CGGAGTTGAC
 241 CGCGTTCATC GGGGCTTCTC CCCATGAGCG CACCGAGACC CGCTCCAATC AGCGCAACGG
 301 CTCGCGTCCG CGCACGCTGT CCACGGTCGC AGGGGACCTG GAACTGCGGA TTCCCAAGCT
 361 GCGCACCGGG TCATTTTTCC CGGCGTTGTT GGAGCGGCGT CGCCGGGTCG ATCAGTGCTT
 421 GTTCGCGGTG GTGATGGAGG CCTACCTGCA CGGCACCTCC ACCCGCAAGG TCGACGATCT
 481 GGTCAAGGCA CTGGGTACCG ATACCGGGAT CTCCAAAAGC GAGGTCAGCC GGATCTGCAA
 541 AGACCTCGAC ACCGAGGTCG CGGCCTTCCG GGACCGGCCG TTGGGTGATC AGCGCTTTCC
 601 GTATGTCTTC CTCGACGCCA CCTACTGCAA GGCCCGGGTG AATCATCGGG TGGTGTCGCA
 661 GGCGGTGGTC ATCGCCACCG GGGTGGCCGC TGACGGGCGC CGCGAGGTAC TGGGCTTTGA
 721 GGTCGGAGAC TCCGAGGACG GGGCGTTCTG GACCGCGTTT TTGCGGTCGT TGAAATCCCG
 781 CGGTCTGGCC GGAGTCCAAC TGGTCATCTC CGATGCCCAT GCCGGACTGC GCAGTGCCAT
 841 TGACGCCGTG CTGATCGGGG CCGCCTGGCA GCGGTGTCGA GTGCACTTCC TGCGCAACGT
 901 GCTCGCCCAA GTGCCCAAGG CTCCGCAGA GATGGTCGCC GCCGCGATCC GCACCGTCTT
 961 CGCCCAGCCA GACGCCGAGC ACGTGCGCGA CAACTCGAC ACCATCGCCG GCATGCTCGG
1021 CCGCCAGTTC CCCAAGGTCG AAACCATGTT GCGCGAGGCC GCCGCCGACA TCACCGCCTT
1081 CGCCGACTTC CCGGTGGCCC ACTGGAAAAA GATCTGGTCA ACCAACCCAC TGGAGCGATT
1141 GAACAAGGAA ATCAAACGCC GCACCGACGT CGTCGGCGTG TTCCCCAACC CCGCCGCGCT
1201 GTTACGGCTG GCCGGCTCGG TACTCGTTGA GGCCCACGAC GAATGGCAGG TCGCCGACAA
1261 GCGCTACCTC TCCGAGACCA GCCTCGCTCT GCTCGACGTC AGTGACCAAA GTGCCGAAAC
1321 CATTGCCCCC ACAGCCGCTC TCACGGCATA GTGGCTACCA CAGAGCCACA CGCGGACACG
1381 CGACCGCTCT TACACCACTC CACGGGACGT GACC
```

FIGURE 2

```
  1 GTCGACGCCA CCACACTGCC CCACGACATC GAACGTCCTG GCCGGCACGA TCGCGAAGGC
 61 GGGAACGGTT GTCGGGCAGC GAATTCTCGT GGGTCGGCCA CTGGTCGGGA ACGCCCGTTG
121 GCTGGCCATT CACGAAGGAG TGGGTGCTCA CCCGCGAACC TTCCACAATG GGGCATGGCT
181 CCATTGGCGC CCGGCGAAAA GGACGCCGCT GATCCGCGCG GTCATCAAAG GTGAGCCCAG
241 CTTTGAACTC CAGCTCGACG TGGCATTCGA CGGCGCGCCA TCGAACGGGC CAGCACGCCA
301 TGCCAGGTCA CCTGATGATC GCGAATGAAG CGCGGTTCGC GCCATACCGT ACGTGCTGGC
361 CCGGCCACCC GGTGTCGTGA CAGCACCGGT GTTCGGCGCG ATCCAACTAG CCTGAGGCAC
421 CACCGACCGC GCGGGCGATG TGGTTCGCTG GGCGCCGCAT GGAAAACGTG CGCGCTGCCG
481 TCGGGCAAAA CCTTCGGGCC ACGAGATTAA TCGGAACCCA TCCACCCCTG TCGGATGAAC
541 CGGTCCGAAT TCGCAGGTAA CGTTCCCGGC GCGCCTGCTG GCCGACGGGA ACGAGCCTTT
601 CACCTGCTCC ATTCCCGTTC TTCACACCCT CCCCGGTTCA ACGGCCGTGC CGCGGCGAGA
661 CCACGCACGA TCACGGTGGC CGCGTCGTGC GACAGGCCCG GCATCGAGTG TCCCGGCCGG
721 CGACCGTATC GCGCCTCGAA GCGGTCGAGG AAGGCCTGTC CGACCGTGTT GCGCTCGTCG
781 TAGCTGTCCA GGCCGATCCA TCCGGATAGG TGCCGCCTCC ACTCCGCGCT GATGTGTGCC
841 ATTCGAACG CCGTCGTCGT GTATCGCGGC GGATCC
```

FIGURE 3

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agatgtccga caccacaaca                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agaccctggg agtgcagata                                                     20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tccagggcga ccgtcgctac                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctggtcaag gcactgggta                                                     20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acctcaaagc ccagtacctc g                                                   21

<210> SEQ ID NO 6
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 6
agccggatct gcaaagacct cgac                                            24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccattcccg ttcttcacac                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttcgaaatg gcacacatca                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
taggtgccgc ctccactccg                                                 20

<210> SEQ ID NO 10
<211> LENGTH: 2809
<212> TYPE: DNA
<213> ORGANISM: Mycobacterium avium

<400> SEQUENCE: 10
ggatccgctg tggaccgtcg ccgcccggca cgtcgaggac gcctgcgcgg tgctggacgg      60
ccaccaggtt cccgaaggcg tgtcgccggc cgggcgggtc atcgaactgc ccggcctcgg     120
ccacccgctg ctgccgccgt ggaccgtcgc cgactccggc gcgcacggcg tcaccatgca     180
ggggcatttc acccgatcgc acgtgggcgg caacaacgcc gtgcacggcg gcatgatccc     240
gctctactac gactggctgt tcggcatggt ggtgtccggc gcgaactgtc cacccacgcg     300
caccgccttc ctacacgtgg attaccgcaa cgtcaccccg atcgacgcgc gctgacggc     360 gcacggccgc atcaccgacg tcgacggccg caagatcttc atctccgcta gcatgacggc     420
ggccgacggc acgctgctca gtgaggccac cggcctgatg gtccgcctgc tacccacca     480 gccgtgagag gcaagatgtc cgacaccaca acagcattca cggtaccggc ggtcgcgaag     540
gccgtcgcgg ccgcgattcc cgaccgcgag ctgatcatcc agggcgaccg tcgctacacc     600
taccggcagg tgatcgaacg gtcgaaccgg ctcgccgcgt atctgcactc ccagggtctg     660
ggatgccaca ccgagcgcga ggcgctggcc ggccacgagg tgggccagga cctgctcggc     720
```

```
ctctacgcgt acaacgggaa cgaattcgtc gaagcgctgc tgggcgcctt cgctgcgcgc      780
gtcgccccgt tcaacgtcaa cttccgctac gtcaaaagcg aactgcacta cctgctcgcg      840
gactccgagg cgaccgcgct gatctaccac gcggcgttcg cgccccgggt ggccgagatc      900
ctgcccgagc tgccgcggct tcgggtgctc atccagatcg ccgacgagtc gggcaacgaa      960
ttactcgacg gcgcagtgga ttacgaggac gcgctggcgt cggtgtccgc gcagccacca     1020
ccggtgcggg actgtccgga cgacctgtac gtgctgtaca ccggcggcac cacgggaatg     1080
cccaagggcg tgttgtggcg tcagcacgac atcttcatga catccttcgg ggggcgcaac     1140
ctgatgaccg gcgagccctc gtcgtcgatc gacgagatcg tgcagcgcgc cgcgtctggc     1200
ccggggacca agctgatgat cctgccgccg ctgatccacg gcgcggccca gtggagcgtg     1260
atgacgcgca tcacgaccgg ccagacggtc gtcttcccca ctgtcgtcga ccatttggac     1320
gccgaggacg tggtgcgcac catcgagcgg gaaaaggtca tggtggtgac ggtggtgggt     1380
gacgcgatgg cgcgcccgtt ggtcgcggcc atcgagaagg ggatcgccga cgtgtcgtcg     1440
ctggccgtgg tggccaacgg cggcgcgttg ctgacccccgt tcgtcaagca gcgcttgatc     1500
gaggtgctgc cgaacgcggt ggtcgtcgac ggcgtcgggt cgtcggagac cggggcgcag     1560
atgcaccaca tgtcgacgcc cggggcggtg gcgaccggca ccttcaacgc cggcccggac     1620
accttcgtgg cggccgagga cctgtcgcg atcctgccgc ccgggcacga ggggatgggc      1680
tggttggccc agcgcggcta tgtcccgctc gggtacaagg gcgatgccgc caagaccgcc     1740
aagacctttc cggtcatcga cggggtgcgc tacgcggtgc cgggcgaccg ggcacgccac     1800
cacgccgacg gccatatcga gctgctgggc cgcgactccg tgtgcatcaa ttccggcggc     1860
gagaagattt tcgtcgagga ggtcgagacg gccatcgcgt cgcatcccgc ggtggccgac     1920
gtggtggtgg ccggacggcc gagtgaacgg tggggccagg aagtcgtcgc cgtggtcgcg     1980
ctgtccgacg gcgctgccgt cgacgccgga gaattgatcg cccacgcatc gaattcgctg     2040
gcgcgctaca agcttcccaa ggcgatcgtg ttccgtccgg tgatcgagcg cagcccgtcg     2100
ggcaaggccg attaccggtg ggcgcgcgag caggcggtga acggatgaaa cccgctgggg     2160
ccgagcgctt ttaggctagg agcacaccga tgaagtacca agggcgggtc gcggtggtca     2220
cgggcgccgg ctcgggcatc ggcgggcgc tgacgcaggc gctcaccgcg ggcggcgcgc      2280
atgtcgcggc gtccgacatc gacgacaacg gcctggccga acccaggcg tcgtgcggtc      2340 ccggacaggt cacgccatat cgcgtcgacg tggcggaccg ggatgcggtg ctgggcttcg     2400
ccgatgaggt gcgccgcaag cacggacccg cctcgatggt gttcaacaac gccggcgtcg     2460
acctgttcgc cagcgtggcc gacatgtcct gggagaactt cgactggctg atgggcatca     2520
acgtcggcgg tgtggtcaac gggaccaaag cctttctgcc gcaactcatc gaagccggct     2580
ccgaccggcg gccgtcgcgg ttggtcaacc tgtccagcgc cttcggtctc atcgcggtcc     2640
cctaccaagg ggcctacagc acgtcgaagt tcgcggtgcg cggattcacg gaggccctgc     2700
gccaggagat gatcatcgaa cgccatccgg tgacggtgca ctgcgtgcac cccggagtcg     2760
tgcgtaccaa cttcggcgcc aacatgcgca cctcggacac cgaggatcc               2809
```

<210> SEQ ID NO 11
<211> LENGTH: 1414
<212> TYPE: DNA
<213> ORGANISM: Mycobacterium avium

<400> SEQUENCE: 11

```
ggagcgtccc ggggagtggt gtaagtgatg gcgcgtgtcg gtccctgacg taagag

| | | | | |
|---|---|---|---|---|
| atccgcgtga | gtctctgtgg | tgaaacgacc | aagaatcact accgagagga | acatcgcgat | 120 |
| ggccctggac | cagtctgcct | tgctggaggt | gctcgacgca ctgcgcaccg | ccgatgccgg | 180 |
| tgagcggatc | actcaagccg | ccgaaacgat | ctaccaagcc ttgatcgacg | cggagttgac | 240 |
| cgcgttcatc | gggcttctc | cccatgagcg | caccgagacc cgctccaatc | agcgcaacgg | 300 |
| ctcgcgtccg | cgcacgctgt | ccacggtcgc | agggacctg gaactgcgga | ttcccaagct | 360 |
| gcgcaccggg | tcatttttcc | cggcgttgtt | ggagcggcgt cgccgggtcg | atcagtgctt | 420 |
| gttcgcggtg | gtgatggagg | cctacctgca | cggcacctcc acccgcaagg | tcgacgatct | 480 |
| ggtcaaggca | ctgggtaccg | ataccgggat | ctccaaaagc gaggtcagcc | ggatctgcaa | 540 |
| agacctcgac | accgaggtcg | cggccttccg | ggaccggccg ttgggtgatc | agcgctttcc | 600 |
| gtatgtcttc | ctcgacgcca | cctactgcaa | ggcccgggtg aatcatcggg | tggtgtcgca | 660 |
| ggcggtggtc | atcgccaccg | gggtggccgc | tgacgggcgc cgcgaggtac | tgggctttga | 720 |
| ggtcggagac | tccgaggacg | gggcgttctg | gaccgcgttt ttgcggtcgt | tgaaatcccg | 780 |
| cggtctggcc | ggagtccaac | tggtcatctc | cgatgcccat gccggactgc | gcagtgccat | 840 |
| tgacgccgtg | ctgatcgggg | ccgcctggca | gcggtgtcga gtgcacttcc | tgcgcaacgt | 900 |
| gctcgcccaa | gtgcccaagg | gctccgcaga | gatggtcgcc gccgcgatcc | gcaccgtctt | 960 |
| cgcccagcca | gacgccgagc | acgtgcgcga | acaactcgac accatcgccg | gcatgctcgg | 1020 |
| ccgccagttc | cccaaggtcg | aaaccatgtt | gcgcgaggcc gccgccgaca | tcaccgcctt | 1080 |
| cgccgacttc | ccggtggccc | actggaaaaa | gatctggtca accaacccac | tggagcgatt | 1140 |
| gaacaaggaa | atcaaacgcc | gcaccgacgt | cgtcggcgtg ttccccaacc | ccgccgcgct | 1200 |
| gttacggctg | gccggctcgg | tactcgttga | ggcccacgac gaatggcagg | tcgccgacaa | 1260 |
| gcgctacctc | tccgagacca | gcctcgctct | gctcgacgtc agtgaccaaa | gtgccgaaac | 1320 |
| cattgccccc | acagccgctc | tcacggcata | gtggctacca cagagccaca | cgcggacacg | 1380 |
| cgaccgctct | tacaccactc | cacgggacgt | gacc | 1414 |

<210> SEQ ID NO 12
<211> LENGTH: 876
<212> TYPE: DNA
<213> ORGANISM: Mycobacterium avium

<400> SEQUENCE: 12

| | | | | |
|---|---|---|---|---|
| gtcgacgcca | ccacactgcc | ccacgacatc | gaacgtcctg gccggcacga | tcgcgaaggc | 60 |
| gggaacggtt | gtcgggcagc | gaattctcgt | gggtcggcca ctggtcggga | acgcccgttg | 120 |
| gctggccatt | cacgaaggag | tgggtgctca | cccgcgaacc ttccacaatg | gggcatggct | 180 |
| ccattggcgc | ccggcgaaaa | ggacgccgct | gatccgcgcg tcatcaaaag | gtgagcccag | 240 |
| ctttgaactc | cagctcgacg | tggcattcga | cggcgcgcca tcgaacgggc | cagcacgcca | 300 |
| tgccaggtca | cctgatgatc | gcgaatgaag | cgcggttcgc gccataccgt | acgtgctggc | 360 |
| ccggccaccc | ggtgtcgtga | cagcaccggt | gttcggcgcg atccaactag | cctgaggcac | 420 |
| caccgaccgc | gcgggcgatg | tggttcgctg | gcgccgcat ggaaaacgtg | cgcgctgccg | 480 |
| tcgggcaaaa | ccttcgggcc | acgagattaa | tcggaaccca tccaccccctg | tcggatgaac | 540 |
| cggtccgaat | tcgcaggtaa | cgttcccggc | gcgcctgctg gccgacggga | acgagccttt | 600 |
| cacctgctcc | attcccgttc | ttcacaccct | ccccggttca acggccgtgc | cgcggcgaga | 660 |
| ccacgcacga | tcacggtggc | cgcgtcgtgc | gacaggcccg gcatcgagtg | tccgggccgg | 720 |
| cgaccgtatc | gcgcctcgaa | gcggtcgagg | aaggcctgtc cgaccgtgtt | gcgctcgtcg | 780 |

```
tagctgtcca ggccgatcca tccggatagg tgccgcctcc actccgcgct gatgtgtgcc    840
atttcgaacg ccgtcgtcgt gtatcgcggc ggatcc                              876
```

ASSAY FOR *MYCOBACTERIUM AVIUM/INTRACELLULARE* NUCLEIC ACID

CROSS-REFERENCE TO RELATED APPLICATIONS

This application is a continuation of U.S. application Ser. No. 11/338,431, filed Jan. 23, 2006, now U.S. Pat. No. 7,824,858, hereby incorporated by reference.

FIELD OF THE INVENTION

The present invention relates to methods and nucleotide sequences for detecting nucleic acids in a sample from *Mycobacterium avium* (*M. avium*) and *Mycobacterium intracellulare* (*M. intracellulare*).

BACKGROUND OF THE INVENTION

*Mycobacterium avium* complex (MAC) disease emerged early in the epidemic of AIDS as one of the common opportunistic infections afflicting human immunodeficiency virus-infected patients. *M. avium* was well known to mycobacteriologists decades before AIDS and known to cause disease, albeit uncommon, in humans and animals. The interaction of MAC with the immune system is complex, and putative MAC virulence factors appear to have a direct effect on the components of cellular immunity, including the regulation of cytokine expression and function. (C. B. Inderlied, et al., Clin Microbiol Rev 6:266-310, 1993).

The genus *Mycobacterium* contains approximately 50 species. The best known and widest spread diseases caused by mycobacteria are leprosy, caused by *M. leprae*, and tuberculosis caused by *M. tuberculosis*. Most other mycobacteria normally occur only as environmental saprophytes. However, saprophytic mycobacterial species also cause opportunist diseases, which happens often, but not exclusively, in individuals suffering from suppressed immune systems, such as AIDS patients or individuals undergoing immuno-suppression therapy. The opportunist strains comprise the slow-growing species *M. avium*, and the closely related *M. intracellulare* and *M. scrofulaceum* (often together referred to as the MAIS complex), *M. kansai*, *M. marinum* and *M. ulcerans*, and the fast-growing species *M. chelonae* and *M. fortuitum*. Although quite rare in the Western world for several decades, the occurrence of opportunist mycobacterial diseases and tuberculosis has shown a significant increase with the incidence of AIDS.

*M. avium* and *M. intracellulare* are two species that together, form the MAC. Because of poor phenotypic differences, conventional culture and biochemical tests give little information to separate these two closely related and nearly indistinguishable species. Therefore the two are commonly referred to as MAC. These opportunistic pathogens are found in water, dust, soil and bird droppings which can enter the body through ingestion of food or water or inhalation through the lungs. Most people usually have small numbers of these bacteria growing in their gut or lungs, but do not have any symptoms. A weakened immune system allows the bacteria to attack the lining of the gut and multiply. From there, infection can disseminate by entering into the blood and spreading through the body. The symptoms of MAC can include weight loss, fevers, chills, night sweats, swollen glands, abdominal pains, diarrhea and overall weakness.

A rapid diagnosis of MAC infection has important clinical and therapeutic implications because of the heightened susceptibility in AIDS patients. Also, MAC infection is not confined and disseminates to a wide variety of organs. A sensitive clinical diagnosis to distinguish between *M. avium*, *M. intracellulare* and other mycobacterial species allows for more precise knowledge of which MAC components are involved in clinical infections and could give better insight into the relevance that these species have as human pathogens. The prognosis of pulmonary diseases may be worse when they are associated with *M. avium* than when they are associated with *M. intracellulare*. (S. Yamori, et al., Chest 102:89-90, 1992). Consequently, differential diagnosis of MAC infections or infections caused by other mycobacteria is important for patient management, antimicrobial treatment, and epidemiology. (J. Kulski, et al., Journal of Clinical Microbiology 34:1985-91, 1996).

Earlier efforts aimed at differentiating among strains of MAC on a nucleic acid level largely failed due to remarkable internal heterogeneity of organisms within the complex suggesting that MAC probably contains several unknown taxonomic groups. (M. C. Menendez, et al., J Clinical Microbiology 39:4241-46, 2001). Wide genetic diversity existing among the members of MAC complicate species-specific identification. (T. Koivula, et al., Microbes and Infection 6:1320-25, 2004).

Polymerase chain reaction (PCR) has been widely utilized to improve sensitivity of standard hybridization methods. Hybridization assays using self-quenching fluorescence probes with or without internal controls for detection of nucleic acid amplification products are known in the art, for example, U.S. Pat. Nos. 6,258,569; 6,030,787; 5,952,202; 5,876,930; 5,866,336; 5,736,333; 5,723,591; 5,691,146; and 5,538,848.

U.S. Pat. No. 6,136,529 describes a method which uses PCR targeting of the 16S rRNA to distinguish MAC organisms from other mycobacteria in test samples. Bruijnesteijn van Coppenraet, et al., J. Clin. Microbiol. 42(6): 2644-50, 2004 report the detection of *M. avium* using Real-time PCR (Taqman® systems). Other methods for detecting mycobacterial nucleic acids that have been reported include Menendez et al., "Characterization of a *Mycobacterium intracellulare* Variant Strain by Molecular Techniques" J. Clin. Microbiol. 39:4241-46, 2001 and Koivula et al., "Genetic diversity in clinical isolates of *Mycobacterium avium* complex from Guinea-Bissau, West Africa" Microbes and Infection 6:1320-25, 2004.

SUMMARY OF THE INVENTION

Provided herein are methods and sequences for detecting MAC nucleic acids, *M. avium* and *M. intracellulare* in a sample. This method is accomplished through assaying a nucleic acid-containing sample for two different gene sequences, one sequence is characteristic of *M. avium* and the other is primarily characteristic of *M. intracellulare*.

Generally it is preferred that detection of the first gene is indicative of the presence of *M. avium* nucleic acids whereas detection of the second gene is indicative of *M. intracellulare*, *M. avium* serovar 2, or *M. avium* serovar 3 nucleic acids. The two gene sequences detected are preferably from different genes.

In one approach, the sample is assayed for the presence or absence of target sequences from the two different genes by amplification and detection of the resulting amplification products. In a preferred embodiment, amplification of target nucleic acids is accomplished by polymerase chain reaction (PCR).

Amplification of the two genes can be performed simultaneously in a single reaction vessel. In this case, the probes may be distinguishably labeled. Alternatively, the assay could be performed in parallel in separate reaction vessels. In such later case, the probes could have the same label.

In a preferred embodiment, the gene sequence that is characteristic of *M. avium* is from the macrophage-induced gene (mig), while the gene sequence that is characteristic of *M. intracellulare*, *M. avium* serovar 2, or *M. avium* serovar 3 is from the DT1 gene. If the sample is positive for both mig and DT1, then *M. avium* of either serovar 2 or 3 is present in the sample, but not *M. intracellulare*. In another preferred embodiment, the gene sequence that is characteristic of *M. avium* is from the insertional sequence transposase gene (IS1245). The IS1245 gene may also be found in *M. paratuberculosis*, however, *M. paratuberculosis* is generally only found in cattle. Therefore, IS1245 is a suitable gene for detecting the presence of *M. avium* in human samples. Preferably, the genes targeted for detection are not the 16S rRNA gene.

In one approach, the present invention provides a method of detecting if a sample contains nucleic acid from *Mycobacterium avium* (*M. avium*) or *Mycobacterium intracellulare* (*M. intracellulare*), the method including detecting a first target nucleic acid sequence specific for *M. avium* and detecting a second target nucleic acid sequence specific for *M. intracellulare* where the first and second target nucleic acid sequences are from different genes. In one embodiment, each target nucleic acid sequence is amplified and then detected.

In a further embodiment, the amplified regions are detected by hybridizing to an oligonucleotide probe having the sequence set forth in SEQ ID NO:3, SEQ ID NO:9 or SEQ ID NO:9 in the presence of an enzyme that cleaves the probe when the probe hybridizes to the target nucleic acid. The probe is preferably conjugated to a detectable label that generates an increased detectable signal upon cleavage. The method further involves detecting a signal from the detectable label, where an increased signal from the detectable label indicates the presence of nucleic acids in the sample. Additional exemplary probes hybridize to a region of the mig sequence (SEQ ID NO:10) between about nucleotides 517 to 536, 524 to 543, 545 to 564, 557 to 576, 595 to 615 and 614 to 633. Additional exemplary probes hybridize to a region of the IS1245 sequence (SEQ ID NO:11) between about nucleotides 502 to 521, 512 to 530, 527 to 550, 551 to 570, 564 to 582, 581 to 600 and 668 to 691. Additional exemplary probes hybridize to a region of the DT1 sequence (SEQ ID NO:12) between about nucleotides 630 to 650, 637 to 656, 648 to 668, 671 to 690, 685 to 705, 704 to 724, 727 to 746, 745 to 764, 767 to 788 and 797 to 816. It is understood that other probes can be used for the present invention. One of ordinary skill in the art could design other probes appropriate in this context.

In another aspect, the present invention provides a method for diagnosing infection of a subject with *Mycobacterium avium* (*M. avium*) or *Mycobacterium intracellulare* (*M. intracellulare*), by contacting a biological sample containing nucleic acids from the subject with a first oligonucleotide specific for a first target nucleic acid sequence of *M. avium*, and a second oligonucleotide specific for a second target nucleic acid sequence of *M. intracellulare*; and determining if the first or second oligonucleotide has hybridized to the sample nucleic acids. The first and second target nucleic acid sequences are preferably from different genes and hybridization of the first oligonucleotide is indicative of infection by *M. avium* while hybridization of the second oligonucleotide is indicative of infection by *M. intracellulare*.

Also provided are oligonucleotides useful in the method and kits containing the oligonucleotides.

Oligonucleotide primers may be designed for amplifying regions of the *M. avium* genome. In one approach, a primer pair is designed to hybridize to a specified segment of the mig gene, GenBank Accession No. U43598. The sequence of exemplary such oligo primers are shown highlighted in FIG. 1 (SEQ ID NO:10). Exemplary primer pairs for amplifying a region of the mig sequence are between about nucleotides 495 to 659; more specifically using a forward primer, SEQ ID NO:1 (5'-AGATGTCCGACACCACAACA-3') and a reverse primer, SEQ ID NO:2 (5'-AGACCCTGGGAGTGCAGATA-3') to amplify a 165 bp region of *M. avium* nucleic acid. Other preferred oligonucleotide primers are approximately 15-100 nucleotides in length and comprise a portion of SEQ ID NO:1 or SEQ ID NO:2. Still other preferred oligonucleotide primers include an oligonucleotide sequence that hybridizes to the complement of a 15-100 nucleotide sequence that comprises the complement of a portion of SEQ ID NO:1 or SEQ ID NO:2. Such oligonucleotides may be substantially purified.

In another approach, a primer pair is designed to hybridize to a specified segment of the mig gene, GenBank Accession No. L33879. The sequence of exemplary such oligonucleotide primers are shown highlighted in FIG. 2 (SEQ ID NO:11). Exemplary primer pairs for amplifying a region of the mig sequence are between about nucleotides 478 to 723; more specifically using a forward primer, SEQ ID NO:4 (5'-TCTGGTCAAGGCACTGGGTA-3') and a reverse primer, SEQ ID NO:5 (5'-ACCTCAAAGCCCAGTAC-CTCG-3') to amplify a 246 bp region of *M. avium* nucleic acid. Other preferred oligonucleotide primers are approximately 15-100 nucleotides in length and comprise a portion of SEQ ID NO:4 or SEQ ID NO:5. Still other preferred oligonucleotide primers include an oligonucleotide sequence that hybridizes to the complement of a 15-100 nucleotide sequence that comprises the complement of a portion of SEQ ID NO:4 or SEQ ID NO:5. Such oligonucleotides may be substantially purified.

Oligonucleotide primers may be designed for amplifying regions of a *M. intracellulare* genome. In one approach, a primer pair is designed to hybridize to a specified segment of the DT1 gene with unknown function, GenBank Accession No. L04543. The sequence of exemplary such oligo primers are shown highlighted in FIG. 3 (SEQ ID NO:12). One example is to use a primer pair to amplify a region of the DT1 sequence between about nucleotides 608 to 849; more specifically using a forward primer, SEQ ID NO:7 (5'-TCCAT-TCCCGTTCTTCACAC-3') and a reverse primer, SEQ ID NO:8 (5'-GTTCGAAATGGCACACATCA-3') to amplify a 242 bp region of *M. intracellulare* nucleic acid. Other preferred nucleotide primers are approximately 15-100 nucleotides in length and comprise a portion of SEQ ID NO:7 or SEQ ID NO:8. Still other preferred oligonucleotide primers include an oligonucleotide sequence that hybridizes to the complement of a 15-100 nucleotide sequence that comprises the complement of a portion of SEQ ID NO:7 or SEQ ID NO:8. Such oligonucleotides may be substantially purified. Table 1 shows the sequence of exemplary primers and probes for amplifying and detecting a region of the mig gene, the IS1245 gene and the DT1 gene.

TABLE 1

Primer/probes for amplifying and detecting regions of the *M. avium* mig gene, the *M. avium* IS1245 gene and the *M. intracellulare* DT1 gene.

| Sequence Name | SEQ ID NO: | Sequence |
| --- | --- | --- |
| Forward Oligonucleotide Primer for *M. avium* (MIGL_01) | SEQ ID NO: 1 | 5'-AGATGTCCGACACCACAACA-3' |
| Reverse Oligonucleotide Primer for *M. avium* (MIGR_01) | SEQ ID NO: 2 | 5'-AGACCCTGGGAGTGCAGATA-3' |
| Oligonucleotide Probe for *M. avium* (MIGP_01FT) | SEQ ID NO: 3 | 5'-TCCAGGGCGACCGTCGCTAC-3' |
| Forward Oligonucleotide Primer for *M. avium* (IS1245L_01) | SEQ ID NO: 4 | 5'-TCTGGTCAAGGCACTGGGTA-3' |
| Reverse Oligonucleotide Primer for *M. avium* (IS1245R_01) | SEQ ID NO: 5 | 5'-ACCTCAAAGCCCAGTACCTCG-3' |
| Oligonucleotide Probe for *M. avium* (IS1245P_01) | SEQ ID NO: 6 | 5'-AGCCGGATCTGCAAAGACCTCGAC-3' |
| Forward Oligonucleotide Primer for *M. intracellulare* (DT1L_01) | SEQ ID NO: 7 | 5'-TCCATTCCCGTTCTTCACAC-3' |
| Reverse Oligonucleotide Primer for *M. intracellulare* (DT1R_01) | SEQ ID NO: 8 | 5'-GTTCGAAATGGCACACATCA-3' |
| Oligonucleotide Probe for *M. intracellulare* (DTIP_01TT) | SEQ ID NO: 9 | 5'-TAGGTGCCGCCTCCACTCCG-3' |

SEQ ID NO:1, SEQ ID NO:4 and SEQ ID NO:7 can be used as forward PCR amplification primers for amplifying a region of MAC nucleic acid. SEQ ID NO:2, SEQ ID NO:5 and SEQ ID NO:8 can be used as reverse PCR amplification primers for amplifying a region of MAC nucleic acid.

SEQ ID NO:3, SEQ ID NO:6 and SEQ ID NO:9 can be used as an oligonucleotide probe to detect the target gene or an amplified sequence thereof. The probe may be labeled. Other oligonucleotide probes can be designed which are between about 10 and about 100 nucleotides in length and hybridize to the amplified region. Oligonucleotide probes are preferably 15-70 nucleotides in length; more preferably 15-60 nucleotides in length; and most preferably 15-25 nucleotides in length.

As used herein, the term "MAC" refers to DNA and/or RNA containing a contiguous sequence from a *Mycobacterium avium* complex genome, or the complement thereof. MAC consists of two predominant species, *M avium* and *Mycobacterium intracellulare*. More than 95% of infections in patients with AIDS are caused by *M avium*, while 40% of infections in immunocompetent patients are caused by *M intracellulare*. MAC is also sometimes called MAI, which stands for *Mycobacterium avium* intracellulare.

As used herein, the term "sample" or "test sample" refers to any liquid or solid material which can contain nucleic acids. In preferred embodiments, a test sample is obtained from a biological source (i.e., a "biological sample"), such as cells in culture or a tissue sample from an animal, more preferably, a human. Preferred sample sources include, but are not limited to, sputum (processed or unprocessed), bronchial alveolar lavage (BAL), bronchial wash (BW), blood, bone marrow, bodily fluids, cerebrospinal fluid (CSF), urine, plasma, serum or tissue (e.g., biopsy material). More preferred samples include sputum, BAL, BW, CSF and urine. The term "patient sample" as used herein refers to a tissue sample obtained from a human seeking diagnosis or treatment of a disease related to MAC infection.

As used herein, the term "oligonucleotide" refers to a short polymer composed of deoxyribonucleotides, ribonucleotides or any combination thereof. Oligonucleotides are generally between about 10 and about 150 nt in length, more preferably about 15 to about 150 nt, more preferably about 15 to about 70 nt, and most preferably between about 20 to about 26 nt. The single letter code for nucleotides is as described in the U.S. Patent Office Manual of Patent Examining Procedure, section 2422, table 1. In this regard, the nucleotide designation "R" means guanine or adenine, "Y" means thymine (uracil if RNA) or cytosine; and "M" means adenine or cytosine. An oligonucleotide may be used as a primer or as a probe.

As used herein, the term "detecting" used in context of detecting a signal from a detectable label to indicate the presence of MT complex nucleic acids in the sample does not require the method to provide 100% sensitivity and 100% specificity. As is well known, "sensitivity" is the probability that a test is positive, given that the person has the disease, while "specificity" is the probability that a test is negative, given that the person does not have the disease. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length, more preferably 18-50 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "target nucleic acid" or "target sequence" as used herein refer to M. avium and M. intracellulare sequences to be amplified and detected. These include the original M. avium or M. intracellulare nucleic acid to be amplified which includes either the coding or complementary strand and either strand of a copy of the original sequence which is produced by the amplification reaction. Copies of the target sequence which are generated during the amplification reaction are referred to as amplification products, amplimers, or amplicons. Target sequences may be composed of segments of a chromosome, a complete gene with or without intergenic sequence, segments or portions of a gene with or without intergenic sequence, or sequence of nucleic acids which probes or primers are designed. Target nucleic acids may include a wild type sequences, a nucleic acid sequence containing a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be native DNA or a PCR amplified product.

"Genomic nucleic acid" or "genomic DNA" refers to some or all of the DNA from a chromosome. Genomic DNA may be intact or fragmented (e.g., digested with restriction endonucleases by methods known in the art). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

The term "flanking" as used herein means that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced from there.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-6, 858, 860 passim; Zhong, et al., Biotechniques 2001 April; 30(4): 852-6, 858, 860 passim.

The term "multiplex PCR" as used herein refers to amplification of two or more products which are each primed using a distinct primer pair.

As used herein, a "primer" for amplification is an oligonucleotide that specifically anneals to a target nucleotide sequence. The 3' nucleotide of the primer should be identical to the target sequence at a corresponding nucleotide position for optimal amplification. The term "primer" as used herein includes all forms of primers that may be synthesized including peptide nucleic acid primers, locked nucleic acid primers, phosphorothioate modified primers, labeled primers, and the like.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, sequences that have "high sequence identity" have identical nucleotides at least at about 50% of aligned nucleotide positions, preferably at least at about 58% of aligned nucleotide positions, and more preferably at least at about 76% of aligned nucleotide positions.

As used herein "TaqMan® PCR detection system" refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

As used herein, "about" means plus or minus 10%.

BRIEF DESCRIPTION OF THE FIGURES

FIG. 1. Nucleotide sequence of Genbank Accession No. U43598 of the mig gene (SEQ ID NO:10) showing the preferred locations for hybridizing PCR primers (shaded regions corresponding to SEQ ID NO:1 and SEQ ID NO:2), and a preferred location for a hybridizing probe (bold underlined corresponding to SEQ ID NO:3).

FIG. 2. Nucleotide sequence of Genbank Accession No. L33879 of the insertion sequence transposase gene (SEQ ID NO:11) showing the preferred locations for hybridizing PCR primers (shaded regions corresponding to SEQ ID NO:4 and SEQ ID NO:5), and a preferred location for a hybridizing probe (bold underlined corresponding to SEQ ID NO:6).

FIG. 3. Nucleotide sequence of GenBank Accession No. L04543 of the DT1 gene (SEQ ID NO:12) showing the preferred locations for hybridizing PCR primers (shaded regions corresponding to SEQ ID NO:7 and SEQ ID NO:8), and a preferred location for a hybridizing probe (bold underlined corresponding to SEQ ID NO:9).

DETAILED DESCRIPTION OF THE INVENTION

In accordance with the present invention, there are provided methods for determining whether a sample contains nucleic acid from *M. avium* and/or *M. intracellulare*.

Sample Preparation

The method may be performed using any biological sample. Biological samples may be obtained by standard procedures and may be used immediately or stored (e.g., the sample may be frozen between about −15° C. to about −100° C.) for later use. The presence of MAC nucleic acids in a sample can be determined by amplifying target regions within MAC nucleic acids. Thus, any liquid or solid material believed to contain MAC nucleic acids can be an appropriate sample. Preferred sample tissues include blood, bone marrow, body fluids, cerebrospinal fluid, urine and others. Heparin is known to inhibit PCR (Beutler, et al. BioTechniques 9:166, 1990), so samples containing heparin are not ideal for the uses contemplated herein. Nucleic acid extraction techniques that remove heparin are known in the art. These techniques may be used to remove heparin from samples to make the samples more suitable for amplification.

Biological samples may be obtained from patients suspected of having a MAC infection, or having any of a wide spectrum of diseases related to MAC infection. MAC is believed to be associated with diseases that have disseminated infections such as association with HIV infection. Less commonly, pulmonary disease in nonimmunocompromised persons is a result of infection with MAC. In children, the most common syndrome is cervical lymphadenitis.

The sample may be processed to release or otherwise make available a nucleic acid for detection as described herein. Such processing may include steps of nucleic acid manipulation, e.g., preparing a cDNA by reverse transcription of RNA from the biological sample. Thus, the nucleic acid to be amplified by the methods of the invention may be genomic DNA, cDNA, single stranded DNA or mRNA.

Nucleic acids from *M. avium* or *M. intracellulare* may be extracted from biological samples prior to amplification. Samples are pre-treated to lyse the mycobacteria, releasing the nucleic acids. Viscous samples such as sputum are generally liquefied by adding a solution of N-acetyl-1-cysteine (NALC) that is resuspended in a solution of citrate and NaOH. Addition of this solution to the sputum breaks it up and liquefies it. Alternatively, viscous samples are treated with DTT, incubated at 65° C. for 30 minutes, centrifuged, and the supernatant removed. Once the sample is liquefied, bacteria are pelleted, resuspended in a neutralizing buffer, and then can be subjected to lysis and nucleic acid extraction.

In an alternate pre-treatment protocol, lysis buffer (MagNA Pure System, Roche) is added in an equal volume of lysis buffer to the sputum. The sample is mixed by vortex and incubated for 15 min at 95° C. At this point, the sputum is sufficiently broken down (the viscosity is decreased enough to pipette), and it can be transferred to an automated DNA extraction instrument (e.g., MagNA Pure). Lysis of the mycobacteria can also be achieved by various methods known in the art (e.g., treatment with proteinase K and lysis buffer, freeze-thaw cycling, or sonication) (Buck et al. J. Clin. Microbiol. 30:1331-1334, 1992). Various commercial nucleic acid purification kits, such as MagNA Pure LC DNA Isolation Kit III or Total Nucleic Acid Isolation Kit (Roche) and related methods known to the skilled artisan and may be used to isolate MAC nucleic acids from the pre-treated samples.

Amplification of Nucleic Acids

Target samples or isolated nucleic acids may be amplified by various methods known to the skilled artisan. Preferably, PCR is used to amplify *M. avium* and/or *M. intracellulare* nucleic acids of interest. In this method, two or more oligonucleotide primers that flank and anneal to opposite strands of a nucleic acid of interest are repetitively annealed to their complementary sequences, extended by a DNA polymerase (e.g., AmpliTaq Gold polymerase), and heat denatured, resulting in exponential amplification of the target nucleic acid sequences. Cycling parameters can be varied, depending on the length of nucleic acids to be extended. The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill. For example, the length of a short nucleic acid or oligonucleotide can relate to its hybridization specificity or selectivity.

Assay controls may be used in the assay for detecting MAC nucleic acid. An internal positive amplification control (IPC) can be included in the sample, utilizing oligonucleotide probes incorporating SEQ ID NO:3, SEQ ID NO:6 or SEQ ID NO:9, and may be introduced as part of a primer/probe mastermix.

Detection of Amplified Nucleic Acids

Amplification of nucleic acids can be detected by any of a number of methods well-known in the art such as gel electrophoresis, column chromatography, hybridization with a probe, or sequencing.

In a preferred approach, a target sequence from each of two genes is amplified in the same reaction vessel. In this case, the amplicon(s) could be detected by first size-separating the amplicons then detection of the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel, (a 2% to 3% agarose gel for about 150 to about 300 base pair amplicons) or a 6% to 10% polyacrylamide gel. The separated nucleic acids can then be stained with a dye such as ethidium bromide and the size of the resulting stained band or bands can be compared to a standard DNA ladder.

In another embodiment, a target sequence from each of two genes is amplified in separate reaction vessels. If the amplification is specific, that is, one target sequence is amplified from one MAC organism but not the other, detection of amplification is sufficient to distinguish between the two types—size separation would not be required.

In some embodiments, amplified nucleic acids are detected by hybridization with a gene-specific probe. Probe oligonucleotides, complementary to a portion of the amplified target sequence may be used to detect amplified fragments. Amplified nucleic acids for each of the target sequences may be detected simultaneously (i.e., in the same reaction vessel) or individually (i.e., in separate reaction vessels). In preferred embodiments, the amplified DNA is detected simultaneously, using two distinguishably-labeled, gene-specific oligonucleotide probes, one which hybridizes to the first target sequence and one which hybridizes to the second target sequence.

The probe may be detectably labeled by methods known in the art. Useful labels include, e.g., fluorescent dyes (e.g., Cy5®, Cy3®, FITC, rhodamine, lanthamide phosphors, Texas red), 32P, 35S, 3H, 14C, 125I, 131I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

A probe oligonucleotide, complementary to the amplified region of MAC nucleic acid, is used to detect the amplification of MAC nucleic acids. The probe may be detectably labeled by methods known in the art. The binding of a probe to the amplified region of the MAC nucleic acid may be determined by hybridization as is well known in the art. Hybridization may be detected in real time or in non-real time.

One general method for real time PCR uses fluorescent probes such as the TaqMan® probes, molecular beacons and scorpions. Real-time reverse-transcriptase (RT) PCR quantitates the initial amount of the template with more specificity, sensitivity and reproducibility, than other forms of quantitative reverse transcriptase PCR, which detect the amount of final amplified product. Real-time RT-PCR does not detect the size of the amplicon. The probes employed in TaqMan® and molecular beacon technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore).

Suitable fluorescent moieties include the following fluorophores known in the art:
4-acetamido-4'-isothiocyanatostilbene-2,2' disulfonic acid, acridine and derivatives:
  acridine
  acridine isothiocyanate
Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes)
5-(2'-aminoethyl)aminonaphthalene-1-sulfonic acid (EDANS)
4-amino-N-[3-vinylsulfonyl)phenyl]naphthalimide-3,5 disulfonate (Lucifer Yellow VS)
N-(4-anilino-1-naphthyl)maleimide
anthranilamide
Black Hole Quencher™ (BHQ™) dyes (biosearch Technologies)
BODIPY® R-6G, BOPIPY® 530/550, BODIPY® FL
Brilliant Yellow
coumarin and derivatives:
  coumarin
7-amino-4-methylcoumarin (AMC, Coumarin 120)
7-amino-4-trifluoromethylcouluarin (Coumarin 151)
Cy2®, Cy3®, Cy3.5®, Cy5®, Cy5.5®
cyanosine
4',6-diaminidino-2-phenylindole (DAPI)
5',5"-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
Eclipse™ (Epoch Biosciences Inc.)
eosin and derivatives:
  eosin
  eosin isothiocyanate
erythrosin and derivatives:
  erythrosin B
  erythrosin isothiocyanate
ethidium
fluorescein and derivatives:
  5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
  fluorescein
  fluorescein isothiocyanate (FITC)
hexachloro-6-carboxyfluorescein (HEX)
  QFITC(XRITC)
  tetrachlorofluorescein (TET)
fluorescamine
IR144
IR1446
Malachite Green isothiocyanate
4-methylumbelliferone
ortho cresolphthalein
nitrotyrosine
pararosaniline
Phenol Red
B-phycoerythrin, R-phycoerythrin
o-phthaldialdehyde
Oregon Green®
propidium iodide
pyrene and derivatives:
  pyrene
  pyrene butyrate
  succinimidyl 1-pyrene butyrate
QSY® 7, QSY® 9, QSY® 21, QSY® 35 (Molecular Probes)
Reactive Red 4 (Cibacron® Brilliant Red 3B-A)
rhodamine and derivatives:
  6-carboxy-X-rhodamine (ROX)
  6-carboxyrhodamine (R6G)
  lissamine rhodamine B sulfonyl chloride
  rhodamine (Rhod)
  rhodamine B
  rhodamine 123
  rhodamine green
  rhodamine X isothiocyanate
  sulforhodamine B
  sulforhodamine 101
  sulfonyl chloride derivative of sulforhodamine 101 (Texas Red)
  N,N,N',N'-tetramethyl-6-carboxyrhodamine (TAMRA)
  tetramethyl rhodamine
  tetramethyl rhodamine isothiocyanate (TRITC)
riboflavin
rosolic acid
terbium chelate derivatives Other fluorescent nucleotide analogs can be used, see, e.g., Jameson, Meth. Enzymol. 278:363-390, 1997; Zhu, Nucl. Acids Res. 22:3418-3422, 1994. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, Mol. Cell. Probes 9:145-156, 1995.

Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, e.g., Cy3® or Cy5® and then incorporated into genomic nucleic acids during nucleic acid synthesis or amplification. Nucleic acids can thereby be labeled when synthesized using Cy3®- or Cy5®-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu, Nat. Biotechnol. 18:345-348, 2000.

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulphur containing side chains of amino acids. See, e.g., U.S. Pat. Nos. 5,580,990; 5,714,327; and 5,985,566; and European Patent No. 0539466.

The binding of a probe to the marker sequence flanking the tandem repeat region may be determined by hybridization as is well known in the art. Hybridization may be detected in real time or in non-real time.

TaqMan® probes (Heid, et al., 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi, et al., Nature Biotechnology 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

TaqMan® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product. One specific requirement for fluorogenic probes is that there be no G at the 5' end. A 'G' adjacent to the reporter dye quenches reporter fluorescence even after cleavage.

Other methods of probe hybridization detected in real time can be used for detecting amplification of MAC nucleic acids. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target sequence, the probe is unfolded, the quencher is moved from the fluorophore, and the resultant fluorescence can be detected.

Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC) and the like. Suitable quenchers include tetra-methylcarboxyrhodamine (TAMRA) 4-(4-dimethylaminophenylazo) benzoic acid ("DABCYL" or a DABCYL analog) and the like. Tetramethylrhodamine (TMR) or 5-carboxyrhodamine 6G (RHD) may be combined as donor fluorophores with DABCYL as quencher. Multiplex TaqMan® assays can be performed using multiple detectable labels each comprising a different donor and quencher combination. Probes for detecting amplified sequence in real time may be stored frozen (−10° to −30° C.) as 100 M stocks. TaqMan® probes are available from Applied BioSystems (4316032).

In a preferred embodiment, real time PCR is performed using TaqMan® probes in combination with a suitable amplification/analyzer such as the ABI Prism 7900HT Sequence Detection System. The ABI PRISM® 7900HT Sequence Detection System is a high-throughput real-time PCR system that detects and quantitates nucleic acid sequences. Briefly, TaqMan® probes specific for each allele are included in the PCR assay. These probes contain a reporter dye at the 5' end and a quencher dye at the 3' end. Each allele specific probe is conjugated with a different fluorescent reporter dye. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation.

Real Time detection on the ABI Prism 7900HT or 7900HT Sequence Detector monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

To minimize the potential for cross contamination, reagent and mastermix preparation, specimen processing and PCR setup, and amplification and detection are all carried out in physically separated areas. In addition, Uracil-N-Glycosylase is utilized (along with the incorporation of Uracil into PCR amplicons) to eliminate carry over contamination.

The examples below illustrate a standard protocol for performing PCR and analyzing in real time. The TaqMan® system of primer labeling is a preferred method of real time detection of PCR amplicons. The following examples serve to illustrate the present invention. These examples are in no way intended to limit the scope of the invention.

EXAMPLE 1

Primer/Probe Mastermix Preparation

A stock solution of primer and probe mastermix was prepared by mixing each of the stock solutions as shown in Table 1.

TABLE 1

Primer/Probe Mastermix.

|  | μl/reaction | Volume/2000 reactions | Final Concentration per reaction |
|---|---|---|---|
| Sterile Nuclease Free Water | 6.90 | 13.8 ml |  |
| 10x Exo IPC Mix | 5.0 | 10.0 ml | 1x |
| 50x Exo IPC DNA | 1.0 | 2.0 ml | 1x |
| MIGL_01 (100 μM) | 0.25 | 500 μl | 500 nM |
| MIGR_01 (100 μM) | 0.25 | 500 μl | 500 nM |

TABLE 1-continued

Primer/Probe Mastermix.

| | µl/reaction | Volume/2000 reactions | Final Concentration per reaction |
|---|---|---|---|
| MIGP_01FT (100 µM) | 0.05 | 100 µl | 100 nM |
| DT1L_01 (100 µM) | 0.25 | 500 µl | 500 nM |
| DT1R_01(100 µM) | 0.25 | 500 µl | 500 nM |
| DT1P_01TT (100 µM) | 0.05 | 100 µl | 100 nM |
| Total | 14.0 µl | 28.0 ml | |

*Exo IPC: Exogenous internal positive control

The mastermix stock solution was dispensed into 280 µl aliquots. Each aliquot is sufficient for up to 19 reactions. This solution can be stored at −20° C. for one year from the date of preparation.

EXAMPLE 2

Preparation of and DNA Extraction of Samples

Biological samples (e.g., sputum, BAL, CSF, blood, urine or pleural fluid) of a volume of 0.35-0.85 ml were collected. DNA was extracted from controls and biological samples using the MagNA Pure LC automated nucleic acid extraction system (Roche Cat #2 236 931). 250 µl of MagNA pure Lysis buffer followed by 250 µl of control or specimen were placed into a sample tube and mixed thoroughly by vortexing for 10 seconds. The samples were incubated at 25° C. for 30 minutes. The entire volume, 500 µl, was added into the MagNA Pure sample cartridge.

EXAMPLE 3

DNA Amplification

To prepare the final mastermix, 500 µl of ABI 2× Mastermix (ABI #4304437) and 20 µl of AmpliTaq Gold was added to a sample tube. The resulting solution was mixed by pulse vortex and short spun in a microcentrifuge. 40 µl of the solution was dispensed into each well of a 96-well optical reaction plate to be used for PCR. The extracts from each control and clinical sample (10 µl/well) were added to individual wells containing the final mastermix. The sample were mixed by gently pipetting the sample up and down two times. The plate was sealed and transferred to the ABI 7900 Sequence Detector.

The thermocycler conditions were as follows:
Stage 1: Hold at 50° C. for 2 minutes.
Stage 2: Hold at 95° C. for 10 minutes.
Stage 3: Cycle from 95° C. for 15 seconds to 60° C. for 1 minutes, 50 cycles.
Sample volume set at 50 µl.

EXAMPLE 4

Data Analysis

The assay as described has been used to detect MAC nucleic acids in a variety of clinical specimens, including sputum, blood, CSF, BAL and urine. The assay results were reproducible over the course of multiple runs. Method comparison studies performed to detect MAC nucleic acids from samples submitted from patients showing symptoms of MAC infection were performed. This included verification studies which tested PCR efficiency, recovery of positive samples, intra-assay reproducibility, inter-assay reproducibility, limit of detection, target specificity, specimen stability, reagent stability and comparison with conventional culture methods. The results support the conclusion that the real-time PCR format described herein is both sensitive and specific, detecting specimens that were shown to be positive for *M. avium* and/or *M. intracellulare* by culture. In addition, the assay in a real-time PCR format was shown to be more sensitive than non-real time PCR format.

*M. avium* is positively identified if a positive result is obtained for mig and a negative result for DT1, except if *M. avium* is of serovar 2 or 3 in which case DT1 will also be positive. *M. intracellulare* is positively identified if a positive result is obtained for DT1 and a negative result for mig. If the sample is positive for both mig and DT1, then it is *M. avium* of serovar 2 or 3, but it is not *M. intracellulare*. The mig gene is also found in *M. paratuberculosis*, however the present assay methods will not detect *M. paratuberculosis* since neither gastric aspirate or stool are designated specimen types used in the present invention.

To ensure the absence of non-specific PCR inhibition of a sample, an internal positive amplification control (IPC) is included with each specimen. The positive control primers and probe are added with the target and sample primers. The IPC or control amplicon is detected by a probe labeled with VIC as the 5' reporter dye. A sample can be interpreted as negative only if the analysis of the internal positive control indicates that DNA amplification has occurred in the reaction tube.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method for detecting whether a sample contains nucleic acid from *Mycobacterium avium* (*M. avium*) or *Mycobacterium intracellulare* (*M. intracellulare*), said method comprising:
   assessing the presence or absence of a first target nucleic acid in said sample; and
   assessing the presence or absence of a second target nucleic acid in said sample;
   identifying the sample as containing nucleic acid from *M. avium, M. intracellulare,* or *M. avium* serovars 2/3, wherein the presence of said first target nucleic acid indicates that the sample contains *M. avium,* wherein the absence of said first target nucleic acid and the presence of said second target nucleic acid indicates that the sample contains *M. intracellulare,* and wherein the presence of said first and second target nucleic acids indicates that the sample contains *M. avium* serovar 2 or *M. avium* serovar 3,
   wherein said first target nucleic acid is specific for the insertion sequence transposase (IS1245) gene of *M. avium* and said second target nucleic acid is specific for the DT1 gene of *M. intracellulare, M. avium* serovar 2 and *M. avium* serovar 3 and
   wherein said sample is not a gastric aspirate or a stool sample.

2. A method according to claim 1, wherein said assessing the presence or absence of said first and second target nucleic acids further comprises amplifying said first and said second target nucleic acids.

3. A method according to claim 1, wherein said assessing the presence or absence of said first and said second target nucleic acid occurs in the same reaction vessel.

4. A method according to claim 1, wherein said assessing the presence or absence of said target nucleic acid further comprises:
   amplifying a region of the *M. avium* IS1245 gene with a first pair of primers resulting in a first amplified region when *M. avium* nucleic acids are present in said sample;
   amplifying a region of the *M. intracellulare, M. avium* serovar 2 or *M. avium* serovar 3 DT1 gene with a second pair of primers resulting in a second amplified region when *M. intracellulare, M. avium* serovar 2 or *M. avium* serovar 3 nucleic acids are present in said sample; and
   assessing the presence or absence of said first and second amplified regions with a corresponding first gene-specific probe and a second gene-specific probe;
   wherein the presence of said first amplified region indicates the presence of said first target nucleic acid and wherein the presence of said second amplified region indicates the presence of said second target nucleic acid.

5. A method according to claim 4, wherein said probes are distinguishably labeled.

6. A method according to claim 4, wherein said first pair of primers comprises a primer comprising the nucleotide sequence of SEQ ID NO: 4, SEQ ID NO: 5, or full complements thereof.

7. A method according to claim 4, wherein said second pair of primers comprises a primer comprising the nucleotide sequence of SEQ ID NO: 7, SEQ ID NO: 8, or full complements thereof.

8. A method according to claim 4, wherein said first gene-specific probe comprises the sequence set forth in SEQ ID NO: 6, or full complements thereof.

9. A method according to claim 4, wherein said assessing the presence or absence of said first and second said amplified regions comprises:
   a) hybridizing at least one of said amplified regions with at least one of said corresponding gene-specific probes wherein said gene-specific probe is an oligonucleotide probe in the presence of an enzyme that cleaves said probe when said probe hybridizes to said corresponding amplified region, wherein said probe is conjugated to a detectable label that generates an increase in its detectable signal upon said cleavage; and
   b) detecting a signal from said detectable label, wherein an increased signal from said detectable label indicates the presence of said corresponding amplified region.

10. A method according to claim 9, wherein said oligonucleotide probe comprises the sequence set forth in SEQ ID NO: 6, SEQ ID NO: 9, or full complements thereof.

11. A method according to claim 9, wherein said oligonucleotide probe hybridizes to said amplified region of the *M. avium* IS1245 gene and said probe is labeled with a fluorescent reporter dye and a quencher dye.

12. A method according to claim 1, wherein said sample is biological and selected from the group consisting of sputum, bronchial alveolar lavage, bronchial wash, blood, bone marrow, bodily fluid, cerebrospinal fluid, urine, plasma, serum or tissue.

13. A method for diagnosing a subject infected with *Mycobacterium avium* (*M. avium*) or *Mycobacterium intracellulare* (*M. intracellulare*), comprising:
   contacting a biological sample containing nucleic acids from the subject with a first oligonucleotide specific for a first target nucleic acid and a second oligonucleotide specific for a second target nucleic acid; and
   determining if said first or second oligonucleotide has hybridized to said sample nucleic acids,
   diagnosing the subject as infected with *M. avium, M. intracellulare,* or *M. avium* serovar 2/3 wherein hybridization of the first oligonucleotide is indicative of infection by *M. avium,* hybridization of the second oligonucleotide but not the first oligonucleotide is indicative of infection by *M. intracellulare,* and hybridization of the first and second oligonucleotides is indicative of infection by *M. avium* serovar 2 or *M. avium* serovar 3; and
   wherein said first target nucleic acid is specific for the IS1245 gene of *M. avium* and said second target nucleic acid is specific for the DT1 gene of *M. intracellulare, M. avium* serovar 2 and *M. avium* serovar 3 and
   wherein said sample is not a gastric aspirate or stool sample.

14. A method according to claim 13, wherein said determining of hybridization further comprises amplifying said first and said second target nucleic acid.

15. A method according to claim 13, wherein said determining of hybridization of said first and said second target nucleic acid occurs in the same reaction vessel.

16. A method according to claim 13, wherein prior to contacting said nucleic acids from the subject with said first and second oligonucleotides further comprises:
- amplifying a region of the *M. avium* IS1245 gene with a first pair of primers when *M. avium* nucleic acids are present in said sample resulting in a first amplified region;
- amplifying a region of the *M. intracellulare, M. avium* serovar 2 or *M. avium* serovar 3 DT1 gene with a second pair of primers when *M. intracellulare, M. avium* serovar 2 or *M. avium* serovar 3 nucleic acids are present in said sample resulting in a second amplified region; and
- wherein said resulting first and second amplified regions correspond to said first and second target nucleic acids.

17. A method according to claim 16, wherein said first pair of primers comprises a primer comprising the sequence of SEQ ID NO: 4, SEQ ID NO: 5, or full complements thereof.

18. A method according to claim 16, wherein said second pair of primers comprises a primer comprising the sequence of SEQ ID NO: 7, SEQ ID NO: 8, or full complements thereof.

19. A method according to claim 16, wherein said first oligonucleotide comprises the sequence set forth in SEQ ID NO: 6 or a full complement thereof, or wherein said second oligonucleotide comprises the sequence set forth in SEQ ID NO: 9 or a full complement thereof.

20. The method of claim 16, wherein said determining of hybridization comprises:
- a) hybridizing at least one of said amplified regions with an oligonucleotide probe in the presence of an enzyme that cleaves said probe when said probe hybridizes to said corresponding amplified region, wherein said probe is conjugated to a detectable label that generates an increase in its detectable signal upon said cleavage; and
- b) detecting a signal from said detectable label, wherein an increased signal from said detectable label indicates the presence of said corresponding amplified region.

21. A method according to claim 13, wherein said oligonucleotides are distinguishably labeled.

22. The method of claim 13, wherein said biological sample is selected from the group consisting of sputum, bronchial alveolar lavage, bronchial wash, blood, bone marrow, bodily fluid, cerebrospinal fluid, urine, plasma, serum or tissue.

* * * * *